US005709864A

United States Patent [19]
Andre et al.

[11] Patent Number: 5,709,864
[45] Date of Patent: Jan. 20, 1998

[54] COSMETIC OR PHARMACEUTICAL AND PARTICULARLY DERMATOLOGICAL, COMPOSITION CONTAINING AN EXTRACT OF TEPHROSIA, PARTICULARLY *TEPHROSIA PURPUREA*

[75] Inventors: Patrice Andre, Neuvilles aux Bois; Sylvie Darnault, Orleans; Isabelle Renimel, Trainou, all of France

[73] Assignee: Parfums Christian Dior, Paris, France

[21] Appl. No.: 596,164

[22] PCT Filed: Jul. 28, 1994

[86] PCT No.: PCT/FR94/00956

§ 371 Date: Jan. 26, 1996

§ 102(e) Date: Jan. 26, 1996

[87] PCT Pub. No.: WO95/03780

PCT Pub. Date: Feb. 9, 1995

[30] Foreign Application Priority Data

Jul. 28, 1993 [FR] France ................... 93 09283

[51] Int. Cl.⁶ ..................................... A61K 35/78
[52] U.S. Cl. .............. 424/195.1; 514/844; 514/888; 514/909
[58] Field of Search ............ 424/195.1; 514/844, 514/888, 909

[56] References Cited

U.S. PATENT DOCUMENTS

| | | | |
|---|---|---|---|
| 4,373,023 | 2/1983 | Langer et al. | 435/2 |
| 4,863,611 | 9/1989 | Bernstein et al. | 210/661 |
| 4,882,318 | 11/1989 | Vlodavsky et al. | 514/56 |
| 4,897,348 | 1/1990 | Johnson et al. | 435/69 |
| 5,211,850 | 5/1993 | Shettigar et al. | 210/645 |

FOREIGN PATENT DOCUMENTS

WO 91/02977  3/1991  WIPO.

OTHER PUBLICATIONS

Anisowicz, Anthony; Bardwell, Lee; Sager, Ruth; Constitutive overexpression of a growth-regulated gene in transformed Chinese hamster and human cells, Proc. Natl. Acad. Sci. USA, vol. 84, pp. 7188–7192, Oct. 1987.

Ausubel, Frederick M; Brent, Roger; Kingston, Robert E; Moore, David D; Seidman, JG; Smith, John A; Struhl, Kevin; Short Protocols In Molecular Biology, Second Edition, John Wiley & Sons, publishers pp. 16–49.

Baldwin, Eric T; Franklin, Kathy A; Appella Ettore; Yamada, Masaaki; Matsushima, Kouji; Wlodawer, Alexander; Weber, Irene T.; Crystallization of Human Interleukin–8, The Journal of Biological Chemistry, vol. 265, No. 12, pp. 6851–6853, 1990.

Blum, Shulamit; Forsdyke, Ruth E; Forsdyke, Donald R; Three Human Homologs of a Murine Gene Encoding an Inhibitor of Stem Cell Proliferation, DNA and Cell Biology, vol. 9, No. 8, 1990, pp. 589–602.

Castor, CW; Walz, DA; Ragsdale, CG; Hossler, PA; Smith, EM; Bignall, MC; Aaron, BP; Mountjoy, K; Connective Tissue Activation XXXIII. Biologically Active Cleavage Products of CTAP–III From Human Platelets, Biochemical and Physical Research Communications, vol. 163, No. 2, 1989, pp. 1071–1078.

Castor, CW; Ritchie, JC; Scott, ME; Whitney, SL; Connective Tissue Activation XI. Stimulation of Glycosaminoglycan and DNA Formation By a Platelet Factor, Arthritis and Rheumatism, vol. 20, No. 3, 1977, pp. 859–868.

Clore, G. Marius; Appella, Ettore; Yamada, Masaki; Matsushima, Kouji; Gronenborn, Angela M; Three–Dimensional Structure of Interleukin 8 in Solution, Biochemistry 1990, 29, 1689–1696.

Cordella–Miele, Eleonora; Miele, Lucio; Mukherjee, Anil B.; A Novel Transglutaminase–mediated Post–translational Modification of Phospholipase $A_2$ Dramatically Increases Its Catalytic Activity, The Journal of Biological Chemistry, vol. 265, No. 28, 1990, pp. 17180–17188.

DesJarlais, Renee L; Sheridan, Robert P; Seibel, George L; Dixon, J. Scott; Kuntz, Irwin D; Venkataraghavan, R; Using Shape Complementarity as an Initial Screen in Designing Ligands for a Receptor Binding Site of Known Three–Dimensional Structure, J. Med. Chem. 1988, 31, pp. 722–729.

Eitan, Shoshana; Schwartz, Michal; A Transglutaminase That Converts Interleukin–2 into a Factor Cytotoxic to Oligodendrocytes, Science, vol. 261, 2 Jul. 1993, pp. 106–108.

Freed, L.E.; Vunjak–Novakovic, G.V.; Bernstein, H; Cooney, C.L.; Langer, R; Kinetics of Immobilized Heparinase in Human Blood, Annals of Biomedical Engineering, vol. 21, pp. 67–76, 1991.

Godder, K; Vlodavsky, I.; Eldor, A; Weksler, BB; Haimovitz–Freidman, A; Fuks, Z; Heparanase Activity in Cultured Endothelial Cells, Journal of Cellular Physiology 148 pp. 274–280 1991.

Greenberg, Charles S; Birckbichler, Paul J; Rice, Robert H; Transglutaminases: multifunctional cross–linking enzymes that stabilize tissues, The FASEB Journal, 1991 pp. 3071–3077.

Greenberg, Sheryl M; Rosenthal, David S; Greeley, Tammy A; Tantravahi, Ramana; Handin, Robert I; Characterization of a New Megakaryocytic Cell Line: The Dami Cell, Blood, vol. 72, No. 6 1988, pp. 1968–1977.

(List continued on next page.)

*Primary Examiner*—John W. Rollins
*Attorney, Agent, or Firm*—Merchant, Gould, Smith, Edell, Welter & Schmidt, P.A.

[57] ABSTRACT

The present invention relates to a cosmetic or a pharmaceutical composition, in particular a dermatological composition. The composition is characterized in that it comprises a cosmetically or pharmaceutically, and in particular dermatologically, effective quantity of an extract of a plant of genus Tephrosia, in particular an extract of the species *Tephrosia purpurea*. According to the invention, it has been discovered that the extract of the plant of genus Tephrosia is useful in preparing a cosmetic, pharmaceutical, and in particular dermatological composition, presenting body-slimming, pigmenting, anti-aging, or anti-inflammatory activity.

35 Claims, No Drawings

OTHER PUBLICATIONS

Haimovitz-Friedman, Adriana; Falcone, Domenick J; Eldor, Amiram; Schirmacher, Volker; Vlodavsky, Israel, Fuks, Zvi; Activation of Platelet Heparitinase by Tumor Cell-Derived Factors Blood, vol. 78, No. 3 1991 pp. 789–796.

Heinrich, Julia N; Ryseck, Rolf-Peter; MacDonald-Bravo, Heather; Bravo, Rodrigo; The Product of a Novel Growth Factor-Activated Gene, fic, Is a Biologically Active "C—C"-Type Cytokine, Molecular and Cellular Biology, vol. 13, No. 4, 1993, pp. 2020–2030.

Heldin, C.-H; Wasteson, A; Westermark, B; Partial Purification and Characterization of Platelet Factors Stimulating the Multiplication of Normal Human Glial Cells, Exp. Cell Res. 109 (1977) pp. 429–437.

Holt, John C; Harris, Mary E; Holt, Angela M; Lange, Eva; Henschen, Agnes; Niewiarowski, Stefan; Characterization of Human Platelet Basic Protein, a Precursor Form of Low-Affinity Platelet Factor 4 and β-Thromboglobulin, Biochemistry 1986, 15, 1988–1996.

Holt, John C; Rabellino, Enrique M; Gewirtz, Alan M; Gunkel, L. Mark; Rucinski, Boguslaw; Niewiarowski, Stefan; Occurrence of Platelet Basic Protein, a Precursor of Low Affinity Platelet Factor 4 and β-thromboglobulin, in Human Platelets and Megakaryocytes, Exp. Hematol., 16:302–306 (1988).

Kaplan, Karen L; Broekman, M. Johan; Chernoff, Arthur, Lesznik, George R; Drillings, Michael; Platelet α-Granule Proteins: Studies on Release and Subcellular Localization, Blood, vol. 53, No. 4, 1979 pp. 604–618.

Khan, M. Yahiya; Newman, Stuart A; A Rapid Colorimetric Assay for Heparinase Activity, Analytical Biochemistry, 196, 373–376 (1991).

Klein, Udo; von Figura, Kurt; Partial Purification and Characterization of a Heparan Sulfate Specific Endoglucoronidase, Biochemical and Biophysical Research Communications, vol. 73, No. 3, 1976, pp. 569–576.

Kusner, David J; Luebbers, Ellen L; Nowinski, Robert J; Konieczkowski, Martha; King, Charles H; Sedor, John R; Cytokine-and LPS-induced synthesis of interleukin-8 from human mesangial cells, Kidney International vol. 39 (1991) pp. 1240–1248.

Laemmli, UK, Cleavage of Structural Proteins during the Assembly of the Head of bacteriophage T4, Nature vol. 227, Aug. 15, 1970 pp. 680–685.

Langer, R., et al, A System for Heparin Removal, Biomaterials: Interfacial Phenomena and Applications pp. 493–509.

Lipes, Myra A; Napolitano, Monica; Jeang, Kuan-Teh; Chang, Nancy T; Leonard, Warren J; Identification, cloning, and characterization of an immune activation gene, Proc. Natl. Acad. Sci. vol. 85, pp. 9704–9708 1988.

Lowry, Oliver; Rosebrough, Nira J; Farr, A. Lewis; Randall, Rose J; Protein Measurement with the Folin Phenol Reagent, J. Biol. Chem., 193:265–275.

Luckow, Verne, Summers, Max D., Trends in the Development of Baculovirus Expression Victors, Bio/Technology, vol. 6, 1988 pp. 47–55.

Luster, Andrew D; Unkeless, Jay C; Ravetch, Jeffrey V; γ-Interferon transcriptionally regulates an early-response gene containing homology to platelet proteins, Letters to Nature, vol. 315, 1985, pp. 672–676.

Matzner, Yaacov; Vlodavsky, Israel; Bar-Ner, Matia; Ishai-Michaeli, Rivka; and Tauber, Alfred I; Subcellular localization of the paranase in human neutrophils, Journal of Leukocyte Biology, vol. 51, 1992, pp. 519–524.

Miller, Michael D; Hata, Shingo; Malefyt, Rene De Waal; Krangel, Michael S; A Novel Polypeptide Secreted By Activated Human T Lymphocytes, The Journal of Immunology, vol. 143, No. 9 1989 pp. 2907–2916.

Miller, Michael D; Krangel, Michael S; Biology and Biochemistry of the Chemokines: A Family of Cheotactic and Inflammatory Cytokines, Critical Reviews in Immunology, 12(1,2) 1992 pp. 17–46.

Moon, Joseph B and Howe, W. Jeffrey, Computer Design of Bioactive Molecules: A Method for Receptor-Based de Novo Ligand Design, Proteins, Structure, Function, and Genetics 11:314–328 1991.

Moore, Stephen, Pepper, Duncan S and Cash, John D, The Isolation and characterisation of a Platelet-Specific β-Globulin (β-Thromboglobulin) And the Detection of Anti-Urokinase and Antiplasmin Released From Thrombin-Aggregated Washed Human Platelets, Biochemica et Biophysica Acta, 379 1975, pp. 360–369.

Nakajima, Motowo; Irimura, Tatsuro; Nicolson, Garth L; Tumor Metastasis-Associated Heparanase (Heparan Sulfate Endoglycosidase) Activity in Human Melanoma Cells, Cancer Letters, 31 (1986) 277–283.

Nakajima, Motowo; Irimura, Tatsuro; Nicolson, Garth L; A Solid-Phase Substrate of Heparanase: Its Application to Assay of Human Melanoma for Heparan Sulfate Degradative Activity, Analytical Biochemistry 157, 1986 pp. 162–171.

Ogren, Soren and Lindahl, Ulf, Cleavage of Macromolecular Heparin by an Enzyme from Mouse Mastocytoma, The Journal of Biological Chemistry, vol. 250, No. 7, 1975 pp. 2690–2697.

Oldberg, Ake; Heldin, Carl-Henrik; Wasteson, Ake; Busch, Christer; Hook, Magnus, Characterization of a Platelet Endoglycosidase Degrading Heprin-like Polysaccharides, Biochemistry 1980 19, pp. 5755–5762.

Oppenheim, Joost J; Zachariae, Claus O.C.; Mukaida, Naofumi; Matsushima, Kouji; Properties of the Novel Proinflammatory Supergene "Intercrine" Cytokine Family, Annu. Rev. Immunol. 1991, 9:617–48.

Parish, Christopher, Coombe, Deirdre R; Jakobsen, Karen B; Bennett, Francis A; Underwood, P. Anne; Evidence That Sulphated Polysaccharides Inhibit Tumour Metastisis By Blocking Tumour-Cell-Derived Heparanases, Int. J. Cancer, 40, 1987, pp. 511–518.

Poncz, Mortimer; Surrey, Saul; LaRocco, Paul; Weiss, Mitchell J; Rappaport, Eric F; Conway, Theresa M; Schwartz, Elias; Cloning and Characterization of Platelet Factor 4 cDNA Derived From a Human Erythroleukemic Cell Line, Blood, vol. 69, No. 1 1987, pp. 219–223.

Rapraeger, Alan C; Krufka, Alison; Olwin, Bradley B; Requirement of Heparan Sulfate for bFGF-Mediated Fibroblast Growth and Myoblast Differentiation, Reports 1991, 1705–1708.

Sasisekharan, Ram; Bulmer, Mark; Moremen, Kelley W; Cooney, Charles L; Langer, Robert; Cloning and expression of heparinase I gene from Flavobacterium heparinum, Proc. Natl. Acad. Sci., vol. 90, pp 3660–3664, 1993.

Savion, Naphtali; Disatnik, Marie-Helene; Nevo Zvi; Murine Macrophage Heparanase: Inhibition and Comparision with Metastic Tumor Cells, Journal of Cellular Physiology 130:77–84 1987.

Schall, Thomas, J: Jongstra, Jan; Dyer, Bradley J; Jorgensen, Jeffrey; Clayberger, Carol; Davis, Mark M: Krensky, Alan M; A Human T Cell–Specific Molecule is a Member of a New Gene Family, Journal of Imunology, vol. 141, pp. 10018–1025, No. 3 1988.

Sewell, Roger F; Brenchley, Paul EC; Mallick, Netar P; Human mononuclear cells contain an endoglycosidase specific for heparan sulphate glycosaminoglycan demonstrable with the use of specific solid–phase metabolically radiolabelled substrate, Biochem J. 1989 264, pp. 777–783.

Shively, John E; Conrad, H. Edward; Formation of Anhydrosugars in the Chemical Depolymerization of Heparin, Biochemistry, vol. 15, No. 18 1976 pp. 3932–3942.

Tekamp–Olson, Patricia; Gallegos, Carol; Bauer, Diane; McClain, Joyce; Sherry, Barbara; Fabre, Myriam; vanDeventer, Sander; Cerami, Anthony; Cloning and Characterization of cDNAs for Murine Macrophage Inflammatory Protein 2 and its Human Homologues, J. Exp. Med. vol. 172, 1990 pp. 911–919.

Van Damme, Jo; Proost, Paul; Lenaerts, Jean–Pierre; Opdenakker, Ghislain; Structural and Functional Identification of Two Human, Tumor–derived Monocyte Chemotactic Proteins (MCP–2 and MCP–3) Belonging to the Chemokne Family, J. Exp. Med., vol. 176, 1992 pp. 50–65.

Vettel, Ulrike; Bar–Shavit, Rachel; Simon, Markus M; Brunner, Georg; Vlodavsky, Israek; Kramer, Michael D; Coordinate secretion and functional synergism of T cell–associated serine proteinase-1 (MTSP-1) and endoglycosidase(s) of activated T cells, Eur. J. Immunol. 1991 21:2247–2251.

Walz, Alfred; Burgener, Roger; Car, Bruce; Baggiolini, Marco; Kunkel, Steven L; Strieter, Robert M; Structure and Neutrophil–activating Properties of a Novel Inflammatory Peptide (ENA–78) with Homology to Interleukin 8, J. Exp. Med., vol. 174, 1991 pp. 1355–1362.

Walz, Alfred; Dewald, Beatrice; von Tscharner, Vinzenz; Baggiolini, Marco; Effects of the Neutrophil–Activating Peptide NAP–2, Platelet Basic Protein, Connective Tissue–Activating Peptide III, and Platelet Factor 4 on Human Neutrophils, J. Exp. Med. vol. 170, 1989, pp. 1745–1750.

Walz, Alfred; Baggiolini, Marco; A Novel Cleavage Product of β–Thromboglobulin Formed in Cultures of Stimulated Mononuclear Cells Activates Human Neutrophils, Biochemical and Biophysical Research Communications, vol. 159, No. 3, 1989, pp. 969–975.

Wenger, Roland H; Wicki, Andreas N; Walz, Alfred; Kieffer, Nelly; Clemetson, Kenneth J; Cloning of cDNA Coding for Connective Tissue Activating Peptide III From a Human Platelet–Derived λgtII Expression Library, Blood, vol. 73, No. 6, 1989, pp. 1498–1503.

Yahalom, Joachim; Fibach, Eitan; Bar–Tana, Ruth; Fuks, Zvi; Vlodavsky, Israel; Differentiating Human Leukemia Cells Express Heparanase That Degrades Heparan Sulfate in Subendothelial Extracellular Matrix, Leukemia Research, vol. 12, No. 9, pp. 711–717 1988.

Yoshimura, Teizo; Yuhki, Naoya; Moore, Stephen K; Appeall, Ettore; Lerman, Michael I; Leonard, Edward J; Human monocyte chemoattractant protein–1 (MCP–1), FEBS Lett., vol. 244, No. 2, 1989, pp. 487–493.

Zhang, Jie and Snyder, Solomon H., Nitric oxide stimulates auto–ADP–ribosylation of glyceraldehyde–3–phosphate dehydrogenase, Proc. Natl. Acad. Sci., vol. 89, pp 9382–9385.

Pandy, "A Study on an Important Drug Plant Tephrosia Purpurea Pers.", Quart, J. Crude Drug Res., 13 (1975), pp. 65–68.

Rahman, et al., "Hypoglycemic activity of Tephrosea purpurea seeds", Indian J. Med. Res., 81, Apr. 1985, pp. 418–421.

"Preliminary Studies on the In Vitro Antimicrobial Activity of Tephrosea Purpurea" (Agarwal, et al.), Letter to the Editor, vol. 31, No. 4, pp. 284–286.

Green, et al., "Sublines of Mouse 3T3 Cells That Accumulate Lipid", Cell 1 (1974), pp. 113–116.

Pairault, et al., "A study of the adipose conversion of suspended 3T3 cells by using glycerophosphate dehydrogenase as differentiation marker", Proc. Natl. Acad. Sci., USA, vol. 76, No. 10, pp. 5138–5142.

Lowry, et al., "Protein Measurement With the Folin Phenol Reagent", Biol. Chem., 193 (1951), pp. 265–275.

COSMETIC OR PHARMACEUTICAL AND PARTICULARLY DERMATOLOGICAL, COMPOSITION CONTAINING AN EXTRACT OF TEPHROSIA, PARTICULARLY *TEPHROSIA PURPUREA*

The present invention relates essentially to the use of an extract of Tephrosia, in particular *Tephrosia purpurea* for preparing a pharmaceutical composition, in particular a dermatological composition, or as a cosmetic agent, and also to a method of cosmetic treatment constituting an application thereof.

Plants of the genus Tephrosia are subtropical plants widely distributed, in particular in India and in Sri Lanka.

A species of the genus Tephrosia that is particularly preferred in the context of the invention is the plant of the species *Tephrosia purpurea*. It is a perennial plant having a height of 30 cm to 100 cm, giving 4 to 6 seeds per pod, and having red flowers. The species *Tephrosia purpurea* is particularly known in India and it is known essentially in Ayurvedic medicine, i.e. in traditional Indian medicine. Various parts have been used to treat a variety of diseases: bronchial, liver, and kidney diseases, and blood purification (see article by Pandey in Quart. J. Crude Drug Res. 13 (1975), pp. 65–68). Seeds of *Tephrosia purpurea* have also been used for hypoglycemic activity (see article by Rahman et al., in Indian J. Med. Res. 81, April 1985, pp. 418–421). In vitro antimicrobial activity of *Tephrosia purpurea* is also known (see article by Agarwal et al. in Indian J. Physiol. Pharmac., Vol. 31, No. 4, October–December 1987, pp. 284–286) using a root extract in 90% alcohol in a Soxhlet apparatus.

After intensive research on plants of the genus Tephrosia, and in particular of the species *Tephrosia purpurea*, the present inventors have discovered, unexpectedly, that extracts, and in particular extracts of the seeds, of the plant Tephrosia, in particular *Tephrosia purpurea*, present powerful stimulation activity for the enzyme adenylate cyclase. It is known that this enzyme transforms ATP into AMPc and pyrophosphate. Because of this activity, extracts of the genus Tephrosia, in particular of the species *Tephrosia purpurea*, are valuable for an application in cosmetics or in pharmacy, in particular in dermatology, in body-slimming activity, in anti-inflammatory activity, in pigmenting activity by acting on melanocytes, and in anti-aging activity.

Thus, in a first aspect, the present invention covers the use of an extract of a plant of the genus Tephrosia, in particular the species *Tephrosia purpurea*, as an active substance for preparing a pharmaceutical composition, in particular a dermatological composition, presenting activity in stimulating the enzyme adenylate cyclase, body-slimming activity, anti-inflammatory activity, pigmenting activity, and anti-aging activity, in particular when applied topically, optionally in a medium, vehicle, or excipient that is pharmacologically, and in particular dermatologically, acceptable.

The invention also covers the use of an extract of a plant of the genus Tephrosia, in particular of the species *Tephrosia purpurea*, as a cosmetic agent for stimulating the enzyme adenylate cyclase, to obtain a body-slimming effect, to obtain a pigmenting effect, or to obtain an anti-aging effect, in particular when applied topically.

In an advantageous embodiment, the above-specified extract is a seed extract of a Tephrosia plant, in particular a seed extract of the species *Tephrosia purpurea*.

It should be observed that the plant *Tephrosia purpurea* is also known, in particular according to the Napralert® database under the following synonymous names: *Cracca purpurea, Galeduba lanceaefolia, Galeduba purpurea, Galepa tinctoria, Tephrosia galegoides, Tephrosia indigofera, Tephrosia lobata,* and *Tephrosia maxima,* all of which are naturally covered by the present invention.

In an advantageous embodiment, this seed extract is a hydroalcoholic extract with a $C_1$–$C_6$ alcohol that is linear or cyclic branched. A particularly preferred alcohol is methanol or ethanol. The relative proportions of water and alcohol may range over wide limits. Nevertheless, substantially equal volume proportions are preferred.

In a second aspect, the present invention also covers a method of cosmetic treatment for obtaining stimulation of the enzyme adenylate cyclase to obtain a body-slimming effect, to obtain a pigmenting effect, or an anti-aging effect, characterized in that it comprises topical application on the areas concerned of a patient, in particular the epidermis or the hair, of a cosmetically effective quantity of an extract of a plant of the genus Tephrosia, in particular the species *Tephrosia purpurea*, optionally in a cosmetically acceptable excipient, medium, or vehicle.

Advantageously, in any of the preceding aspects, 0.001% to 5%, and preferably 0.01% to 5%, by weight of extract is used relative to the total weight of the composition.

Other objects and advantages of the invention appear clearly in the light of the following explanatory description made with reference to various embodiments of the invention given purely by way of illustration and that do not in any way limit the scope of the invention. Unless specified otherwise, percentages given in the description and the claims are given by weight.

EXAMPLE 1

Making a plant extract from *Tephrosia purpurea*

1000 grams (g) of *Tephrosia purpurea* seeds purchased commercially were taken and ground and passed through a 1 mm screen. The screening was steeped for 24 h in 5 liters (l) of hydroalcoholic extraction solvent constituted in this case by a 50/50 V/V methanol-water mixture.

It was refluxed for 1 h.

It was then filtered on paper (pressure could have been used). It was washed in cold methanol.

The alcohol and the water were then vacuum evaporated off until they had completely disappeared from the filtrate.

The residue was weighed, giving 80.11 g of extract of non-uniform appearance comprising a clear crystalloid and a dark paste.

The raw extract contained about 50% dry matter and 50% residual solvents.

It was suitable for use as such, or it could have been further purified by conventional methods well known to the person skilled in the art.

EXAMPLE 2

2.365 kg of commercially available seeds of the plant *Tephrosia purpurea* were ground and screened with a 1 mm screen, and then degreased with petroleum ether.

The ground and degreased seeds were then subjected to extraction for 2 hours in a Soxhlet apparatus with about 10 l of ethanol.

After the solvent had been evaporated off, a residue was obtained in the form of a brownish gum weighing about 58 g.

EXAMPLE 3

Use of *Tephrosia purpurea* extract to show stimulation of adenylate cyclase activity Certain substances act as intracellular messengers, and as a result they are essential constituent substances of cells that adapt the functioning of cells to the requirements of the organism. Such messengers include 3',5' adenosine which is a cyclic monophosphate (AMPc). This molecule is metabolized from adenosine 3',5'-triphosphate by an enzyme called adenylate cyclase.

The theoretical reaction is as follows:

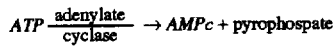

$$ATP \xrightarrow{\text{adenylate cyclase}} AMPc + \text{pyrophospate}$$

Theory

Cell membranes are initially obtained by culturing to confluence fibroblasts of the 3T3 F442A line commercially available from Flow Laboratories.

These fibroblast cell membranes which constitute an enzyme source, are incubated in a reaction medium in the presence of ATP at 37° C. for a predefined length of time.

The resulting AMPc is measured by radioimmunoassay. Taking the basal activity, i.e. activity without an effector, as being 100%, it is possible to determine the influence of an effector on the enzyme system. If the activity is greater than 100%, then there is an activator effect of adenylate cyclase, and if the activity is less than 100%, then on the contrary an inhibitor effect is demonstrated.

Implementation

Cell membranes are purified from the fibroblast in culture.

In this context, it should be observed that purification of cell membranes releases numerous enzymes into the assay medium. Two of these enzymes are undesirable in implementing the test. They comprise firstly $Na^+$, $K^+$ ATPase which transform ATP into adenosine diphosphate, and secondly phosphodiesterase 3',5'-AMPc which degrades cyclic AMP into AMP. Thus, in order to obtain reliable results from the test, it is essential to inhibit those two enzymes. The first is inhibited by means of ouabain, and the second by means of theophylline.

The reaction medium is thus constituted by:

50 µl of a 5 mM solution of adenosine 3',5'-triphosphate (ATP) as substrate;

100 µl of a 20 mM solution of ouabain as an inhibitor of ATPase;

100 µl of a 20 mM solution of theophylline as an inhibitor of phosphodiesterase; and 100 µl of a solution containing 0.05 g/l dry matter of the effector.

After incubation, the reaction is stopped by heating for 10 minutes to 100° C., centrifuging, and recovering the supernatent to measure the AMPc by radioimmunoassay (kit reference 1117 from the French company Immunotech).

Results

The results of tests are given in the table below:

TABLE 1

|  | Basal activity | Positive reference = forskoline at 0.05 g/l | Tephrosia purpurea at 0.05 g/l dry extract from Example 2 |
|---|---|---|---|
| % activity | 100 | 225 | 185 |

It can be seen very clearly from the above results that the extract from the plant Tephrosia purpurea possesses large significant activity in stimulating the enzyme adenylate cyclase. This activity is relatively close to that of the positive reference as constituted by forskoline, even though the plant extract does not contain that molecule.

Thus, Tephrosia extracts, in particular Tephrosia purpurea extracts, constitute an interesting alternative for forskoline in its use in preparing cosmetic or pharmaceutical compositions.

Applications of the present invention are, in particular, those which stem from biological processes in which AMPc plays a role. Of such applications, those preferred in the invention are preparing slimming compositions, pigmenting compositions for the skin or the hair, anti-inflammatory compositions, and compositions for opposing the effects of aging.

EXAMPLE 4

Demonstrating lipolytic activity in the composition of the invention

Evaluating the action of the composition of the invention on adipocytes in culture It was decided to evaluate the effectiveness of compositions of the invention as lipolytic agents on a line of mouse pre-adipocytes, such as a 3T3 F442A line commercially available from Flow Laboratories, which have been selected for their ability to convert into adipocytes if culture conditions make that possible.

(In application of the method of H. Green & C. Kehinde, Cell, 1 (1974), 113.)

This line constitutes a model for studying in vitro adipocyte differentiation while providing the possibility, when the adipocyte phenotype is achieved, of studying extracellular regulation of cell functioning in accordance with the invention. This differentiation, and modulation thereof, are accompanied by a certain number of morphological and biochemical changes, and in particular biochemical changes concerning the release of glycerol during lipolysis.

It is thus convenient to verify the effectiveness of compounds to be tested by measuring the activity of the enzyme glycerol-3-phosphate dehydrogenase (written G3PDH) which is involved in the following lipid generating reaction:

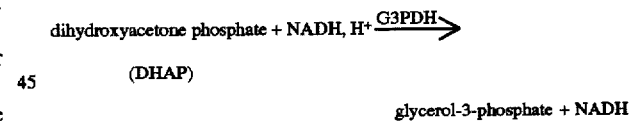

$$\text{dihydroxyacetone phosphate} + NADH, H^+ \xrightarrow{G3PDH} \text{glycerol-3-phosphate} + NADH$$

(DHAP)

Thus, enzyme activity can be measured using the method of assaying the release NADH by the method described by J. Pairault et al. in Proc. Nat. Acad. Sci., Volume 6 (1979), pp. 5138–42.

These experiments were performed as follows:

1) Culture conditions

The pre-adipocytes were seeded in 35 mm diameter Petri dishes (20,000 cells/dish) in the presence of Dulbecco's Modified Eagle Medium (DMEM) containing 5% calf serum, plus 5% fetal calf serum.

The medium was renewed twice with DMEM medium plus 10% fetal calf serum.

Under such conditions, the culture reached confluence in 1 week (D=D0), at which stage adipocyte differentiation was activated by adding insulin at a concentration of 1% by weight of culture medium. There were also two changes of the DMEM culture medium plus 10% fetal calf serum and 1% insulin.

The cells presented an advanced differentiated state 1 week after confluence (D=D7).

2) Treatment-viability

The cells were treated with the substances to be tested at stage D7.

The treatment consisted in replacing the culture medium either by medium only as a reference, or else by the same medium but containing the substance to be tested at various concentrations.

To assay G3PDH activity, the culture medium was recovered 7 days after treatment (D=D14).

3) Assaying G3PDH enzyme activity on day D14

The monolayer of cells was recovered by scraping and it was vigorously homogenized in a 25 mM TRIS-HCl buffer, pH 7.4, with 1 mM EDTA at 4° C. G3PDH activity was assayed on the cell particle supernatent after centrifuging.

The assay, performed using the above-mentioned Pairault assay method, measured G3PDH enzyme activity per milligram of protein. The protein content was determined by the protein assay method described by J. Lowry in Biol. Chem., 193 (1951), pp. 265–75, with enzyme activity being expressed in nanomoles/min/mg of protein.

Three tests were performed per sample or per reference.

The following substances were tested:

a) a first reference substance for which the DMEM medium had added thereto 7.5 µl of ethanol for 6 ml of culture medium;

b) the same medium but having 60 µl of DMSO (dimethylsulfoxide) added to 6 ml of culture medium;

c) the same medium but having added thereto an extract of *Coleus forskohlii* containing forskoline, which is commercially available, at a concentration of 0.025 g/l dry matter diluted in 7.5 µl of ethanol for 6 ml of culture medium;

d) a substance in which the above DMEM medium had added thereto 0.2 g/l dry extract of *Tephrosia purpurea* as obtained from Example 2, diluted in 60 µl of DMSO for 6 ml of culture medium;

e) a substance in which the DMEM medium had added thereto 0.1 g/l dry extract of *Tephrosia purpurea* as obtained from Example 2, diluted in 60 µl of DMSO for 6 ml of culture medium; and f) a substance in which the DMEM medium had added thereto 0.05 g/l dry extract of *Tephrosia purpurea* as obtained from Example 2, diluted in 60 µl of DMSO for 6 ml of culture medium.

The results obtained are given in Table 2 below:

TABLE 2

| Substance under test | G3PDH activity expressed as nanomoles of NADH released per min/ml of protein |
|---|---|
| Ethanol reference | 382.68 |
| DMSO reference | 392.36 |
| *Coleus forskohlii* | 176.48 |
| Tephrosia (0.2 g/l) | 155.23 |
| Tephrosia (0.1 g/l) | 353.03 |
| Tephrosia (0.05 g/l) | 369.64 |

It can be seen very clearly from the results of Table 2 above that the extract of the plant *Tephrosia purpurea* possesses considerable significant activity in inhibiting the activity of G3PDH, as shown by the small quantity of NADH released. In addition, from a concentration 0.02 g/l, this activity is similar or slightly greater than the activity obtained with the extract of *Coleus forskohlii* which contains forskoline, known for its activity in stimulating adenylate cyclase and its effect on lipolyses.

It can be advantageous to inhibit G3PDH activity using a substance that does not contain forskoline, thus providing an alternative of interest to forskoline in its use for preparing cosmetic or pharmaceutical compositions for the activities mentioned above.

The present invention is described below with reference to various examples of formulations for cosmetic or pharmaceutical compositions, in particular dermatological compositions.

EXAMPLE 5

Body slimming cream

*Tephrosia purpurea* seed extract of Example 1  1%

Excipient for cream q.s.p.  100%

This cream is applied at least once a day for 2 to 3 weeks to areas of the body having fatty substances, until the desired slimming effect is obtained.

EXAMPLE 6

Pigmenting cosmetic composition

This composition comprises the following ingredients:

*Tephrosia purpurea* seed extract of Example 1  0.5%

Ordinary cosmetic gel excipient q.s.p.  100%

The gel is applied to areas of the skin that are to be pigmented until the desired effect is obtained.

EXAMPLE 7

Anti-inflammatory pharmaceutical composition, in particular a dermatological composition This composition comprises the following ingredients:

*Tephrosia purpurea* seed extract of Example 1  0.2%

Pharmaceutically acceptable excipient q.s.p.  100%

EXAMPLE 8

Anti-aging cosmetic composition

This composition comprises the following ingredients:

*Tephrosia purpurea* seed extract of Example 1  0.1%

Usual cosmetic excipient q.s.p.  100%

This composition is applied to areas of the skin where an anti-aging effect is sought after, and it is applied for a sufficient period of time, generally of the order of several weeks to several months depending on the subject.

We claim:

1. A method of performing a treatment of body zones selected from the epidermis and the hair, comprising stimulating the enzyme adenylate cyclase by applying on the body zones a stimulating effective amount of an extract of a plant of the genus Tephrosia.

2. The method of claim 1, wherein said plant is of the species *Tephrosia purpurea*.

3. The method of claim 1, wherein said extract is administered as a composition having a concentration of said extract ranging between 0.001% and 5% by weight with respect to the total weight of the composition.

4. The method of claim 1, wherein said extract is an extract obtained by use of an extraction solvent selected from the group consisting of a $C_1$–$C_6$ alcohol and a $C_1$–$C_6$ hydroalcohol.

5. The method of claim 1, wherein the extract is selected from the group consisting of methanol and ethanol.

6. The method of claim 1, wherein said extract is a seed extract.

7. The method of claim 1, wherein said extract is a seed extract of the species *Tephrosia purpurea*.

8. The method of claim 1, wherein said extract is a 50/50 V/V methanol-water solvent extract of *Tephrosia purpurea* seeds.

9. The method of claim 1, wherein said extract is an ethanol extract of the plant *Tephrosia purpurea*.

10. A method for providing a cosmetic effect for a person, comprising delivering to said person an effective amount for said cosmetic effect of an extract of a plant of the genus Tephrosia.

11. The method of claim 10, wherein said cosmetic effect is for slimming.

12. The method of claim 11, wherein said extract is administered as a composition having a concentration of said extract ranging between 0.001% to 5% by weight with respect to the total weight of the composition.

13. The method of claim 10, wherein said cosmetic effect is for pigmenting.

14. The method of claim 10, wherein said cosmetic effect is for reducing signs of aging.

15. The method of claim 10, wherein said cosmetic effect is anti-inflammatory.

16. The method of claim 10, wherein said plant is of the species *Tephrosia purpurea*.

17. The method of claim 10, wherein said extract is administered as a composition having a concentration of said extract ranging between 0.001% to 5% by weight with respect to the total weight of the composition.

18. The method of claim 10, wherein said extract is an extract obtained by use of an extraction solvent selected from the group consisting of a $C_1$–$C_6$ alcohol and a $C_1$–$C_6$ hydroalcohol.

19. The method of claim 18, wherein the solvent is selected from the group consisting of methanol and ethanol.

20. The method of claim 10, wherein said extract is a seed extract.

21. The method of claim 10, wherein said extract is a seed extract of the species *Tephrosia purpurea*.

22. The method of claim 10, wherein said extract is a 50/50 V/V methanol-water solvent extract of *Tephrosia purpurea* seeds.

23. The method of claim 10, wherein said plant is an ethanol extract of the plant *Tephrosia purpurea*.

24. The method of claim 10, comprising applying said extract topically on body zones selected from the epidermis and the hair.

25. A method for performing a pharmaceutical treatment selected from the group consisting of a slimming treatment and an anti-inflammatory treatment on a subject, comprising delivering to the subject an effective amount for said pharmaceutical treatment of an extract of a plant of the genus Tephrosia.

26. The method of claim 25, wherein said plant is of the species *Tephrosia purpurea*.

27. The method of claim 26, wherein said extract is administered as a composition having a concentration of said extract ranging between 0.001% and 5% by weight with respect to the total weight of the composition.

28. The method of claim 25, wherein said extract is administered as a composition having a concentration of said extract ranging between 0.001% and 5% by weight with respect to the total weight of the composition.

29. The method of claim 25, wherein said extract is an extract obtained by the use of an extraction solvent selected from the group consisting of a $C_1$–$C_6$ alcohol and a $C_1$–$C_6$ hydroalcohol.

30. The method of claim 29, wherein the solvent is selected from the group consisting of methanol and ethanol.

31. The method of claim 25, wherein said extract is a seed extract.

32. The method of claim 25, wherein said extract is a seed extract of the species *Tephrosia purpurea*.

33. The method of claim 25, wherein said extract is a 50/50 V/V methanol-water solvent extract of *Tephrosia purpurea* seeds.

34. The method of claim 25, wherein said plant is an ethanol extract of the plant *Tephrosia purpurea*.

35. The method of claim 25, comprising applying said extract topical on body zones selected from the epidermis and the hair.

* * * * *